(12) United States Patent
Arai et al.

(10) Patent No.: US 8,445,712 B2
(45) Date of Patent: May 21, 2013

(54) PHOSPHOLIPID DERIVATIVE AND PH-RESPONSIVE LIPOSOMES

(75) Inventors: Masaya Arai, Kanagawa (JP); Kazuhiro Kubo, Kanagawa (JP); Shoichi Yokoyama, Kanagawa (JP); Kenji Kono, Osaka (JP)

(73) Assignees: NOF Corporation, Tokyo (JP); Osaka Prefecture University Public Corporation, Sakai-shi (JP)

( * ) Notice: Subject to any disclaimer, the term of this patent is extended or adjusted under 35 U.S.C. 154(b) by 0 days.

(21) Appl. No.: 13/509,513

(22) PCT Filed: Nov. 12, 2010

(86) PCT No.: PCT/JP2010/070237
§ 371 (c)(1),
(2), (4) Date: Jun. 25, 2012

(87) PCT Pub. No.: WO2011/059073
PCT Pub. Date: May 19, 2011

(65) Prior Publication Data
US 2012/0258165 A1 Oct. 11, 2012

(30) Foreign Application Priority Data
Nov. 13, 2009 (JP) .................. 2009-260398

(51) Int. Cl.
*C07F 9/24* (2006.01)
(52) U.S. Cl.
USPC ........................................ 558/159
(58) Field of Classification Search
USPC ........................................ 558/159
IPC ........................................ C07F 9/24
See application file for complete search history.

(56) References Cited

U.S. PATENT DOCUMENTS

| 7,495,116 B2 * | 2/2009 | Itoh et al. ................. 554/78 |
| 7,524,981 B2 * | 4/2009 | Kubo et al. ................. 554/78 |
| 2005/0119481 A1 * | 6/2005 | Rehwinkel et al. ........... 544/59 |
| 2005/0220856 A1 | 10/2005 | Itoh et al. |
| 2006/0210618 A1 | 9/2006 | Kubo et al. |

FOREIGN PATENT DOCUMENTS

| JP | 2004-352619 A | 12/2004 |
| JP | 2008-120718 A | 5/2008 |
| WO | WO 03/082882 A1 | 10/2003 |
| WO | WO 2004/060899 A1 | 7/2004 |

OTHER PUBLICATIONS

Japanese Patent Office, International Search Report in International Patent Application No. PCT/JP2007/070237 (Dec. 7, 2010), English translation.

* cited by examiner

*Primary Examiner* — Gollamudi Kishore
*Assistant Examiner* — Celeste A Roney
(74) *Attorney, Agent, or Firm* — Leydig, Voit & Mayer, Ltd.

(57) ABSTRACT

A phospholipid derivative represented by the following formula (1)

$$R^1O-CH_2 \\ R^2O-CH \quad O \quad O \quad O \\ \mid \quad \parallel \quad \parallel \quad \parallel \\ CH_2-OPOCH_2CH_2NHC(CH_2)_aCO-[PG]_{k1} \begin{bmatrix} O & O \\ \parallel & \parallel \\ OC-R^3-COH \end{bmatrix}_{k2} \\ \mid \\ OM \quad [OH]_{k3}$$

(1)

wherein each symbol is as described in the specification; a liposome containing the phospholipid derivative, and the like.

12 Claims, 5 Drawing Sheets

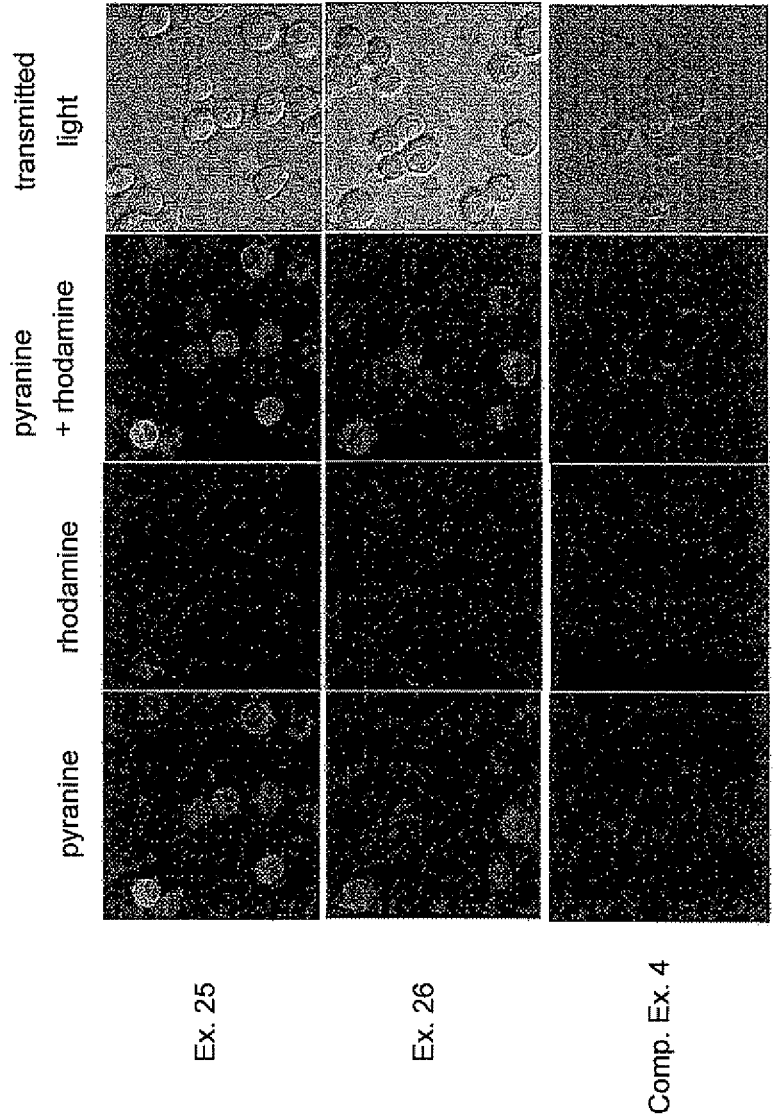

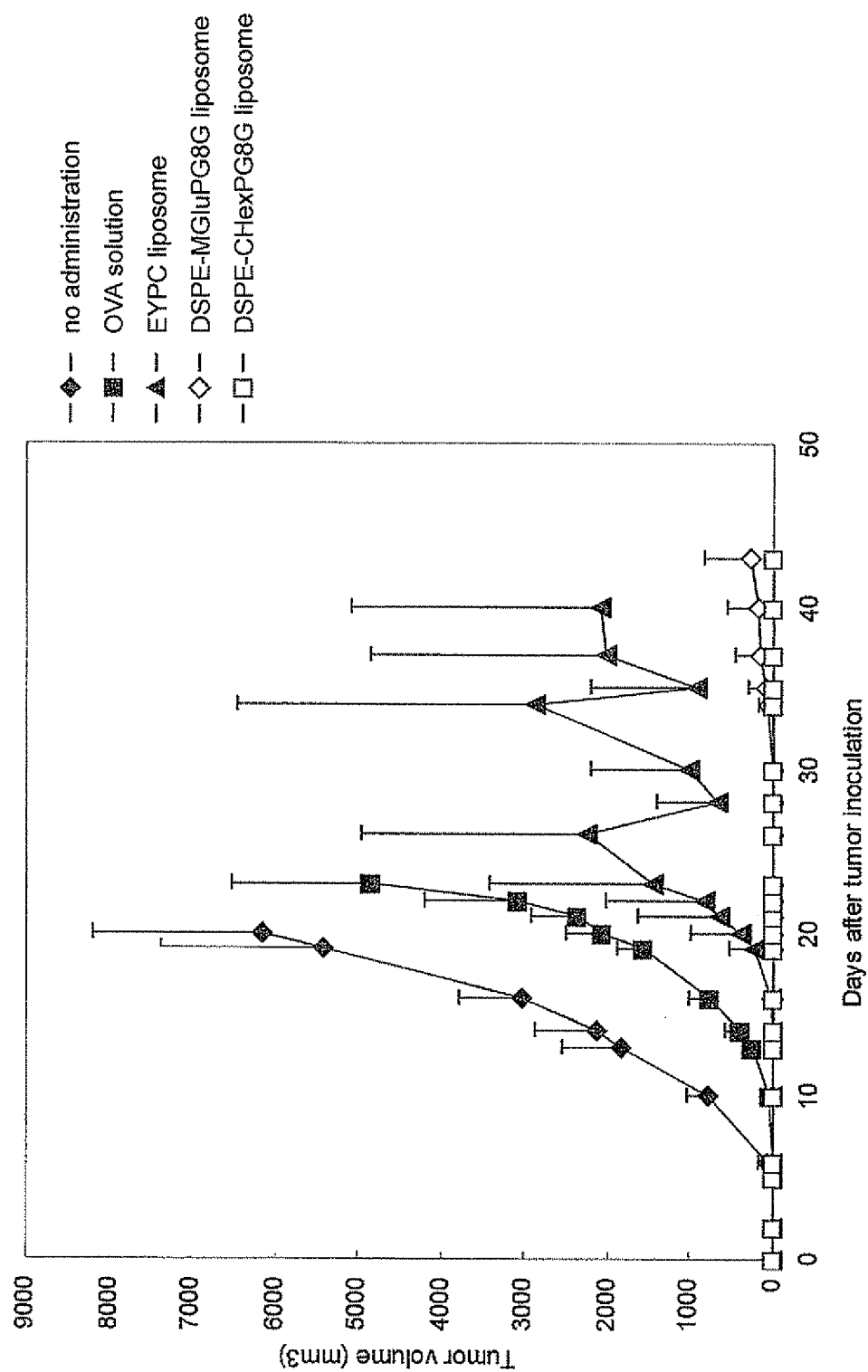

PHOSPHOLIPID DERIVATIVE AND pH-RESPONSIVE LIPOSOMES

CROSS-REFERENCE TO RELATED APPLICATIONS

This patent application is the U.S. national phase of International Patent Application No. PCT/JP2010/070237, filed Nov. 12, 2010, which claims the benefit of Japanese Patent Application No. 2009-260398, filed Nov. 13, 2009, which are incorporated by reference in their entireties.

TECHNICAL FIELD

The present invention relates to a novel phospholipid derivative. In addition, it relates to a liposome having, as a drug delivery system (DDS), pH-sensitiveness that enables release of a substance enclosed therein at a particular pH.

BACKGROUND ART

A drug carrier, wherein a drug is carried on a vector (carrier), is attracting attention as a drug delivery system (hereinafter to be described as "DDS") to certainly, safely and efficiently deliver a drug into the cells of the object lesion site, and has been actively studied. Particularly, when the drug is a physiologically active substance that expresses activity in cells, such as protein, DNA (gene), antisense molecule and the like, the drug needs to be introduced into the cytoplasm to show effective action. However, since cell membrane does not allow permeation of many water-soluble substances and polymers, a vector (carrier) to deliver the drug into the cytoplasm is necessary. Vector includes virus vector and synthetic vector. Since virus vector has safety problems, the development of a safe and highly functional synthetic vector is desired, and use of lipid membrane vesicles such as liposome, emulsion, lipid microsphere and the like has been considered.

Particularly, as the above-mentioned synthetic vector, studies have been made to apply vesicles such as liposome and the like to DDS as a drug carrier. These vesicles are generally prepared from phospholipid or a derivative thereof, sterol, lipid other than phospholipid, and the like as a basic membrane constituent. With these basic constituent components alone, however, problems of coagulation of vesicles, low retention in the body and the like are difficult to solve, and delivery of the drug contained in the liposome to the object site (for example, target organ and cell) as a DDS preparation is difficult. To solve these problems, it has been reported to avoid interaction with blood components, blood cells and vascular endothelial cells by forming a liposome using a polyglycerol phospholipid derivative (for example, patent document 1). However, although this technique maintains retention in blood, the presence of a water-soluble polymer becomes an obstacle that prevents the drug from approaching and contacting the organ or cell to act on, and intracellular introduction rate of the drug becomes problematically low.

Therefore, studies of enhanced introduction into the cell by modification of a liposome membrane with a substance showing an interaction with a biomembrane are also ongoing. For example, a succinylated derivative of polyglycerol (hereinafter to be indicated as SucPG), which shows membrane fusion under mild acidic conditions, has been reported (for example, patent document 2). In addition, it has been reported that a drug carrier wherein a drug is carried on carrier particles of lipid membrane modified by a 3-methylglutaric acid derivative of polyglycerol which has different hydrocarbon chain length from SucPG and a branched structure, and an amidine derivative which is a cationation modifier, has a transgene activity (for example, patent document 3). However, in these derivatives, a hydrocarbon group is introduced into polyglycerol at not desired positions but random positions. Therefore, when these derivatives are used as constituent substances of carrier particles made of lipid membranes such as liposome, the hydrocarbon group to be the anchor part is randomly incorporated into the lipid membrane at plural positions. As a result, hydrophilic polyglycerol chain is restricted and cannot separate much from the liposome surface, thus failing to expand the hydration sphere. Therefore, a stable liposome is difficult to form.

DOCUMENT LIST

Patent Documents patent document 1: WO 2004/060899
patent document 2: JP-A-2004-352619
patent document 3: JP-A-2008-120718

SUMMARY OF THE INVENTION

Problems to be Solved by the Invention

As mentioned above, a drug carrier for DDS, which is capable of certainly targeting a lesion site and efficiently delivering a drug to the object site, is desired. Particularly, when the drug is a physiologically active substance that shows a pharmacological action in the cell, the development of a drug carrier that shows a still more improved cell introduction rate is strongly desired to efficiently express the drug in the cell.

It is therefore an object of the present invention to provide a liposome having pH-sensitiveness as a drug carrier, which is effective as a vector capable of achieving an introduction system that can safely and efficiently transfect a physiologically active substance that expresses activity in a cell, such as protein, antisense molecule, nucleic acid, polynucleotide, gene and analogs thereof and the like, into a cell, a liposome having pH-sensitiveness, which is effective as a carrier for DDS therapy which certainly targets a lesion site such as cancer (e.g., kidney cancer, lung cancer, liver cancer, pancreatic cancer and the like), lymphoma, pneumonia, hepatitis, nephritis, blood vessel endothelial damage site and the like, and safely and efficiently delivers a drug for the treatment and/or diagnosis to the site, and a phospholipid derivative useful for forming such drug carrier.

Means of Solving the Problems

Faced with such problems, the present inventors have elucidated for the first time that a liposome containing a phospholipid derivative represented by the following formula (1)

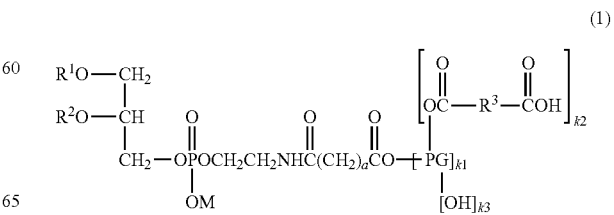

wherein each symbol is as described in the specification, has a fusion activity with a cell membrane since the liposome membrane becomes unstable at a low pH.

The present inventors have further conducted intensive studies based on these findings, which resulted in the completion of the present invention.

Accordingly, the present invention relates to

[1] a phospholipid derivative represented by the following formula (1)

$$R^1O-CH_2$$
$$R^2O-CH$$
$$CH_2-OPOCH_2CH_2NHC(CH_2)_aCO\text{---}[PG]_{k1}$$
$$OM$$
$$\left[\begin{matrix} O & O \\ \| & \| \\ OC-R^3-COH \end{matrix}\right]_{k2}$$
$$[OH]_{k3}$$
(1)

wherein $R^1$ and $R^2$ are each independently an acyl group having 8-24 carbon atoms or an aliphatic hydrocarbon group having 8-24 carbon atoms, $R^3$ is a branched chain or cyclic divalent hydrocarbon group having 2-12 carbon atoms, a is an integer of 0-5, M is a hydrogen atom, an alkali metal or an ammonio group, PG is a residue derived from polyglycerol, k1 is an integer of 2-50, and $k2 \geq k3$ and $k2+k3=k1+1$ are satisfied (hereinafter sometimes to be indicated as "phospholipid derivative (1)");

[2] the phospholipid derivative of [1], wherein $R^1$ and $R^2$ are each independently an acyl group having 12-20 carbon atoms or an aliphatic hydrocarbon group having 12-20 carbon atoms;

[3] the phospholipid derivative of [1] or [2], wherein $R^3$ is a branched chain or cyclic divalent hydrocarbon group having 3 to 8 carbon atoms;

[4] the phospholipid derivative of any one of [1] to [3], wherein $R^3$ is a 2-methylpropylene group or a 1,2-cyclohexene group;

[5] a liposome comprising the phospholipid derivative of any one of [1] to [4];

[6] the liposome of [5], which is pH-sensitive;

and the like.

Effect of the Invention

The phospholipid derivative of the present invention has properties in that it is protonated due to the dibasic acid introduced into the polyglycerol chain to show strong hydrophobicity, when pH is low.

Therefore, the liposome of the present invention containing the phospholipid derivative of the present invention, as a drug carrier, is pH-sensitive and, different from the conventionally-used liposomes, can have a membrane fusion activity since the liposome membrane is unstabilized by decreased pH in the endosome. Therefore, the liposome of the present invention is efficiently fused with the endosome membrane, and can efficiently transfer the content of the liposome into the cytoplasm, thus showing an improved cell introduction rate than known drug carriers.

Such pH-sensitive liposome of the present invention can express membrane fusion property in a lesion site, and can efficiently and safely introduce a drug into an affected area or cell. Therefore, the pH-sensitive liposome of the present invention, which encloses a pharmacologically active substance, a physiologically active substance or a diagnostic substance, is useful as DDS for treatment and diagnostic objects.

BRIEF DESCRIPTION OF THE DRAWINGS

FIG. 4 shows that the liposome of the present invention is taken up by a cell and releases the substance in the liposome.

FIG. 5 shows the results of a tumor rejection test using a liposome dispersion enclosing OVA.

DESCRIPTION OF EMBODIMENTS

1. Phospholipid Derivative

Figure 1:
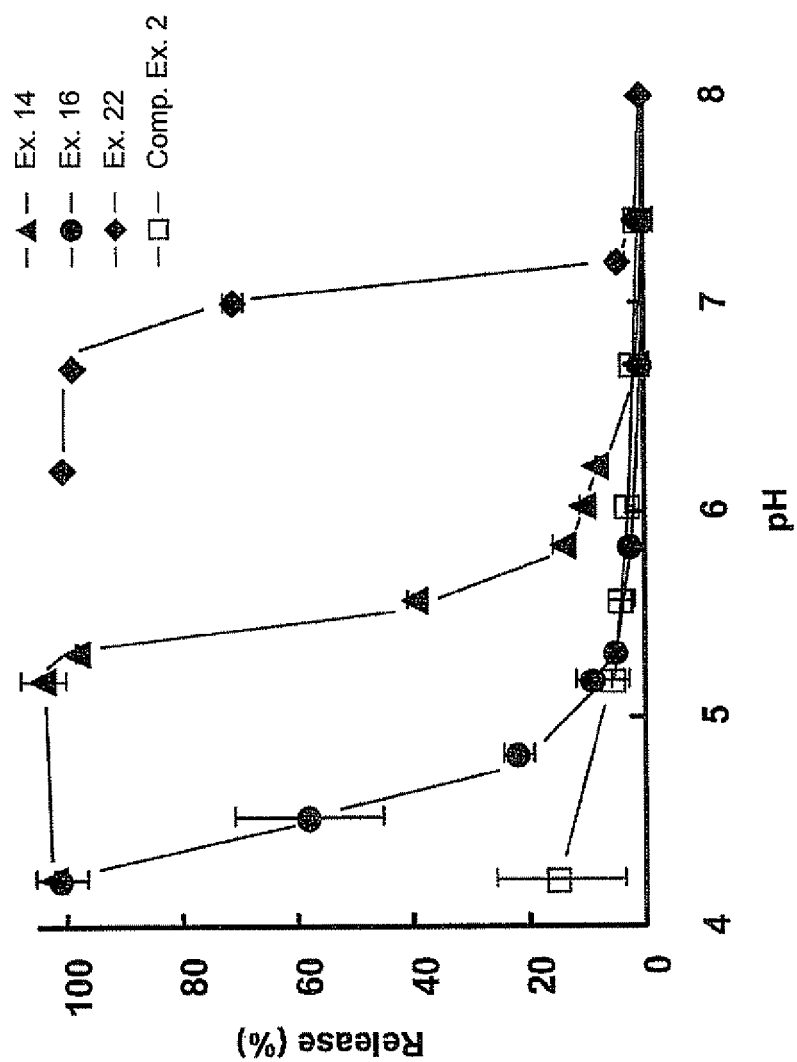
FIG. 1 shows that the liposome of the present invention releases the substance in the liposome in response to pH.

In phospholipid derivative (1), a group represented by $[PG]_{k1}$ is a "polyglycerol-derived residue" having an average polymerization degree k1.

In the present specification, the "polyglycerol-derived residue" for PG means a group obtained by removing all hydroxyl groups from the glycerol repeat units of the polyglycerol. k1 specifically shows the number of the repeat units of the polyglycerol and is not particularly limited. When k1 is less than 2, the hydration sphere is insufficiently formed when the liposome of the present invention is formed mentioned below, and when it exceeds 50, since the hydrophilic polyglycerol skeleton is larger than the phospholipid skeleton, the liposome of the present invention is difficult to form, or the liposome of the present invention when formed is inferior in the stability. Therefore, k1 is preferably 2-50, more preferably 2-20, particularly preferably 3-12.

In phospholipid derivative (1), k2 shows an average number of the substituents derived from a dibasic acid represented by the formula (2)

$$\left[\begin{matrix} O & O \\ \| & \| \\ -OC-R^3-COH \end{matrix}\right]$$
(2)

wherein $R^3$ is as described in the specification (mentioned below), which is bonded to the "polyglycerol-derived residue" having an average polymerization degree k1 which is represented by $[PG]_{k1}$. k2 is generally 2-51.

In phospholipid derivative (1), k3 shows an average number of the hydroxyl groups bonded to the "polyglycerol-derived residue" having an average polymerization degree k1 which is represented by $[PG]_{k1}$. k3 is generally 0-25.

The relationship of k1, k2 and k3 satisfies $k2+k3=k1+1$.

In addition, the relationship of k2 and k3 satisfies $k2 \geq k3$. When k3 is greater than k2, the pH-sensitiveness becomes insufficient. For the liposome of the present invention to express sufficient pH-sensitiveness, k2≧1.25×k3 is preferable, k2≧1.5×k3 is more preferable, and k2≧2×k3 is particularly preferable.

The phospholipid derivative of the present invention has properties in that it is protonated due to the dibasic acid introduced into the polyglycerol chain to show strong hydrophobicity, when pH is low. That is, the pH at which endosome and liposome are membrane-fused to release the content varies depending on the introduction rate of the dibasic acid.

The present inventors have found that, when the liposome composition is the same, as the introduction rate of the dibasic acid introduced into phospholipid derivative (1) becomes lower, the pH-sensitive region shifts toward the acidic side. They have also found that, when the introduction rate of the dibasic acid is the same, as the amount of phospholipid derivative (1) in the liposome composition becomes smaller, the pH-sensitive region shifts toward the acidic side.

As mentioned below, the liposome of the present invention utilizes the mechanism of a substance being taken up by endosome during its transfer from the blood into the cell. The blood has pH of about 7.4, at which pH the liposome needs to stably exist and have drug retention ability. Furthermore, it is known that pH decreases to about 5-6 in the endosome, due to the action of proton pump and the like (e.g., see Taylor&Francis Inc, Bruce Alberts, Molecular Biology of the Cell, vol. 3rd, pages 610-611). In consideration of release of the contents from the liposome, it is preferable to produce a liposome having a membrane fusion activity at least within the range of pH 5-7.

The liposome of the present invention containing the above-mentioned phospholipid derivative (1) is a liposome having a membrane fusion activity within the range of pH 5-7. Furthermore, the liposome of the present invention is a liposome permitting adjustment of a pH-sensitive region, so that the pH-sensitive region can be shifted to the acidic side by decreasing the dibasic acid introduction rate or reducing the amount of phospholipid derivative (1) in the liposome.

The dibasic acid introduction rate in phospholipid derivative (1) is represented by the following numeric formula.

Dibasic acid introduction rate=$k2/(k2+k3)\times 100$

When the introduction rate represented by the numeric formula is not more than 50%, the pH-sensitiveness becomes insufficient. Therefore, in phospholipid derivative (1), $k2/(k2+k3)\times 100>50$ is desirable. Particularly, for the liposome of the present invention to express sufficient pH-sensitiveness, the dibasic acid introduction rate is preferably not less than 56%, more preferably not less than 60%, particularly preferably not less than 67%.

In phospholipid derivative (1), a is an integer of 0-5. When a exceeds 5, hydrophobicity becomes strong and the liposome of the present invention is difficult to form. From the aspect of easy production of the liposome of the present invention, a is preferably 2-4, more preferably 2 or 3, particularly preferably 3.

In phospholipid derivative (1), M is a hydrogen atom, an alkali metal atom or an ammonio group.

In the present specification, examples of the "alkali metal" include lithium, sodium, potassium and the like.

From the aspect of superior preservation stability of phospholipid derivative (1), M is preferably an alkali metal or ammonia, more preferably sodium or ammonia.

In phospholipid derivative (1), $R^1$ and $R^2$ are each independently an acyl group having 8-24 carbon atoms or an aliphatic hydrocarbon group having 8-24 carbon atoms. From the aspect of more easy production of the liposome of the present invention, preferably, $R^1$ and $R^2$ are each independently an acyl group having 12-20 carbon atoms or an aliphatic hydrocarbon group having 12-20 carbon atoms, more preferably an acyl group having 14-18 carbon atoms or an aliphatic hydrocarbon group having 14-18 carbon atoms.

When $R^1$ and $R^2$ are acyl groups, the ester bond moiety is easily hydrolyzed. Therefore, when the liposome of the present invention is used for treatment or diagnosis, it is easily metabolized from the human body. When $R^1$ and $R^2$ are hydrocarbon groups, the liposome of the present invention has superior hydrolysis resistance, and therefore, the liposome solution has superior preservation stability. $R^1$ and $R^2$ can be optionally selected according to the desired property of the liposome of the present invention.

In the present specification, examples of the "acyl group having 8-24 carbon atoms" include a saturated or unsaturated acyl group having 8-24 carbon atoms. Examples of such group include residues obtained by removing a hydroxyl group from caprylic acid, pelargric acid, capric acid, undecanoic acid, lauric acid, tridecanoic acid, myristic acid, pentadecanoic acid, palmitic acid, margaric acid, stearic acid, nonadecanoic acid, arachidic acid, heneicosanic acid, behenic acid, tricosanic acid, lignoceric acid, myristoleic acid, palmitoleic acid, oleic acid, eicosenoic acid, erucic acid, hexadecadienoic acid, linoleic acid, eicosadienoic acid, docosadienoic acid, hexadecatrienoic acid, α-linolenic acid, γ-linolenic acid, eicosatrienoic acid, arachidonic acid, eicosapentaenoic acid, docosatetraenoic acid, docosahexaenoic acid and the like.

Of these, in view of easy handling, strong formation of lipid membrane, and the like, an acyl group having 12-20 carbon atoms is preferable, and an acyl group having 14-18 carbon atoms is more preferable. Among others, residues obtained by removing a hydroxyl group from myristic acid, pentadecanoic acid, palmitic acid, stearic acid, myristoleic acid, arachidic acid, palmitoleic acid, oleic acid, hexadecadienoic acid and linoleic acid are more preferable.

In the present specification, examples of the "aliphatic hydrocarbon group having 8-24 carbon atoms" include a linear, branched chain or cyclic aliphatic hydrocarbon group optionally having one or more unsaturated bonds. Examples of such group include an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an icosyl group, a heneicosyl group, a docosyl group, a tricosyl group, a tetracosyl group, a myristoleyl group, a palmitoleyl group, an oleyl group, an eicosyl group, a hexadienyl group, a linoleyl group, an eicosenyl group, an erucyl group, a γ-linolenyl group, an eicosatrienyl group and the like. Of these, in view of easy handling, strong formation of lipid membrane, and the like, an aliphatic hydrocarbon group having 12-20 carbon atoms is preferable, and an aliphatic hydrocarbon group having 14-18 carbon atoms is more preferable. Among others, a tetradecyl group, a hexadecyl group, an octadecyl group, a myristoleyl group, a palmitoleyl group, an oleyl group and a linoleyl group are more preferable.

In phospholipid derivative (1), $R^3$ is a branched chain or cyclic divalent aliphatic hydrocarbon group having 2-12 carbon atoms. When the carbon number in the group is less than 2, the pH-sensitiveness of the liposome of the present invention is difficult to obtain. On the other hand, when the carbon number exceeds 12, the formation property of the liposome of the present invention becomes inferior due to strong hydrophobicity.

In the present specification, examples of the "branched chain or cyclic divalent hydrocarbon group having 2-12 carbon atoms" include a branched chain or cyclic divalent hydrocarbon group having 2-12 carbon atoms and optionally having one or more unsaturated bond. Examples of such group include branched chain aliphatic hydrocarbon groups such as a methylmethylene group, an ethylmethylene group, a 1-methylethylene group, a 2-methylethylene group, a 1-methyleneethylene group, a 2-methyleneethylene group, a 1,2-dimethylethylene group, a 1,1-dimethylethylene group, a 2,2-dimethylethylene group, a 1-hexen-1-ylethylene group, a 2-hexen-1-ylethylene group, a 1-octenylethylene group, a 2-octenylethylene group, a 1-allylethylene group, a 2-allylethylene group, a 1-butylethylene group, a 2-butylethylene group, a 1-decylethylene group, a 2-decylethylene group, a 1-phenylethylene group, a 2-phenylethylene group, a 1-n-octylethylene group, a 2-n-octylethylene group, a 1-nonenylethylene group, a 2-nonenylethylene group, a 1-methylpropylene group, a 2-methylpropylene group, a 3-methylpropylene group, a 1,1-dimethylpropylene group, a 2,2-dimethylpropylene group, a 3,3-dimethylpropylene group, a 1-ethylpropylene group, a 2-ethylpropylene group, a 3-ethylpropylene group, a 1-ethyl-1-methylpropylene group, a 1,3-diethylpropylene group, a 2-ethylpropylene group, a 2-ethylbutylene group, a 2-propylbutylene group, a 2-(t-butyl)butylene group, a 2,2,6,6-tetramethylpentene group and the like; alicyclic hydrocarbon groups such as a 1,2-cyclohexene group, a 1,3-cyclohexene group, a 1,4-cyclohexene group, a 1-methylene-2,3-cyclopropene group, a 1,2-cyclobutene group, a 1,1-cyclobutene group, a 1,1-cyclopropene group, a 3,4-bicyclo(2.2.1)heptene group, a 2,2-bicyclo(2.2.1)heptene group, a 2,3-bicyclo(2.2.1)heptene group, a 9,10-tricyclo[4.2.1.1(2,5)]decene group, a 2,4-(1-methyl-3-phenyl)bicyclo(1.1.0)butene group, a 9,10-(4-methyl)pentacyclo[4.4.0.0(2,5).0(3,8).0(4,7)]decene group, a 9,10-pentacyclo[4.4.0.0(2,5).0(3,8).0(4,7)]decene group, a 2,4-pentacyclo[4.4.0.0(2,5).0(3,8).0(4,7)]decene group, a 4,4'-biphenylene group, a 2,3-(cis-5-norbornen)yl group, a 1,3-adamantanyl group and the like; and aromatic hydrocarbon groups such as a 1,2-phenylene group, a 1,3-phenylene group, a 1,4-phenylene group, a 1,2-(3-methyl)phenylene group, a 1,2-(4-methyl)phenylene group, a 1,2-(4-ethyl)phenylene group, a 1,2-(4-propyl)phenylene group, a 1,2-(4-n-butyl)phenylene group, a dibutyl-1,2-phenylene group, a 1,2-(4-isobutyl)phenylene group, a 1,3-(5-methyl)phenylene group, a 1,3-(5-ethyl)phenylene group, a 1,3-(5-n-butyl)phenylene group, a 1,3-(5-isobutyl)phenylene group, a 1,3-(5-t-butyl)phenylene group, a 1,2-(4-t-butyl)phenylene group, a 1,2-naphthalenyl group, a 1,4-naphthalenyl group, a 2,3-naphthalenyl group, a 2,6-naphthalenyl group, a 1,8-naphthalenyl group and the like. $R^3$ is preferably a branched chain or cyclic divalent hydrocarbon group having 3 to 8 carbon atoms, more preferably a 2-methylpropylene group or a 1,2-cyclohexene group.

In phospholipid derivative (1), $R^3$ is a branched chain or cyclic divalent aliphatic hydrocarbon group having 2-12 carbon atoms. When the carbon number in the group is less than 2, the pH-sensitiveness of the liposome of the present invention is difficult to obtain. When the carbon number exceeds 12, the formation property of the liposome of the present invention becomes inferior due to strong hydrophobicity.

$R^3$ in phospholipid derivative (1) is a residue obtained by removing two carboxyl groups from a dibasic acid-derived substituent represented by the formula (2)

Examples of the above-mentioned dibasic acid from which $R^3$ may be derived include dibasic acids having a branched chain hydrocarbon group such as methylmalonic acid, ethylmalonic acid, methylsuccinic acid, ethylsuccinic acid, methylenesuccinic acid, 2,2-dimethylsuccinic acid, 2,3-dimethylsuccinic acid, 2-hexen-1-ylsuccinic acid, 2-octenylsuccinic acid, allylsuccinic acid, butylsuccinic acid, decylsuccinic acid, phenylsuccinic acid, n-octylsuccinic acid, nonenylsuccinic acid, 2-methylglutaric acid, 3-methylglutaric acid, 2,2-dimethylglutaric acid, 3,3-dimethylglutaric acid, 2-ethylglutaric acid, 3-ethylglutaric acid, 2-ethyl-2-methylglutaric acid, 2,4-diethylglutaric acid, 3-ethylglutaric acid, 3-methyladipic acid, 3-ethyladipic acid, 3-propyladipic acid, 3-(t-butyl)adipic acid, 2,2,6,6-tetramethylpimelic acid and the like; dibasic acids having an alicyclic hydrocarbon group such as 1,2-cyclohexanedicarboxylic acid, 1,3-cyclohexanedicarboxylic acid, 1,4-cyclohexanedicarboxylic acid, 1-methylenecyclopropane-2,3-dicarboxylic acid, 3-methylenecyclopropane-1,2-dicarboxylic acid, cyclobutane-1,2-dicarboxylic acid, cyclobutane-1,1-dicarboxylic acid, cyclopropane-1,1-dicarboxylic acid, bicyclo(2.2.1)heptane-3,4-dicarboxylic acid, bicyclo(2.2.1)heptane-2,2-dicarboxylic acid, bicyclo(2.2.1)heptane-2,3-dicarboxylic acid, tricyclo[4.2.1.1(2,5)]decane-9,10-dicarboxylic acid, 1-methyl-3-phenyl-bicyclo(1.1.0)butane-2,4-dicarboxylic acid, 4-methylpentacyclo[4.4.0.0(2,5).0(3,8).0(4,7)]decane-9,10-dicarboxylic acid, pentacyclo[4.4.0.0(2,5).0(3,8).0(4,7)]decane-9,10-dicarboxylic acid, pentacyclo[4.4.0.0(2,5).0(3,8).0(4,7)]decane-2,4-dicarboxylic acid, biphenyl-4,4'-dicarboxylic acid, cis-5-norbornane-endo-2,3-dicarboxylic acid, 1,3-adamantanedicarboxylic acid and the like; and dibasic acids having an aromatic hydrocarbon group such as phthalic acid, isophthalic acid, terephthalic acid, 3-methylphthalic acid, 4-methylphthalic acid, 4-ethylphthalic acid, 4-propylphthalic acid, 4-n-butylphthalic acid, dibutylphthalic acid, 4-isobutylphthalic acid, 5-methylisophthalic acid, 5-ethylisophthalic acid, 5-n-butylisophthalic acid, 5-isobutylisophthalic acid, 5-t-butylisophthalic acid, 4-t-butylphthalic acid, 1,2-naphthalenedicarboxylic acid, 1,4-naphthalenedicarboxylic acid, 2,3-naphthalenedicarboxylic acid, 2,6-naphthalenedicarboxylic acid, 1,8-naphthalenedicarboxylic acid and the like. Of these, a dibasic acid having 5 to 10 carbon atoms ($R^3$ has 3 to 8 carbon atoms.) is preferable, and 3-methylglutaric acid and 1,2-cyclohexanedicarboxylic acid are more preferable.

2. Production Method of Phospholipid Derivative (1)

While the production method of phospholipid derivative (1) is not particularly limited, it can be produced by reacting a 1,2-diacyl or 1,2-dialkylphosphatidylethanolamine polyglycerol derivative represented by the following formula (3)

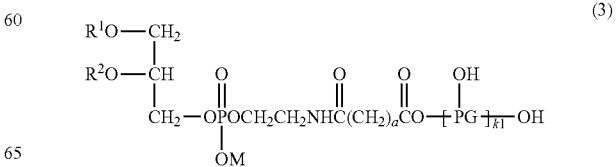

wherein each symbol is as mentioned above (hereinafter sometimes to be described as "compound (3)") with a dibasic acid or an anhydride thereof in an organic solvent.

Compound (3) can be appropriately synthesized according to a compound known per se by those of ordinary skill in the art.

As the dibasic acid to be reacted with compound (3), the dibasic acids recited in the above-mentioned "dibasic acid from which $R^3$ may be derived" can be preferably used. While any of the dibasic acid and anhydride thereof may be used for the reaction, the dibasic acid anhydride is preferably used since mild reaction conditions can be employed and undesirable side reaction and the like can be suppressed.

As an organic solvent to be used for the reaction of compound (3) with the above-mentioned dibasic acid or anhydride thereof, any can be used without any particular limitation as long as it does not have a functional group such as a hydroxyl group and the like. Examples of such organic solvent include ethyl acetate, dichloromethane, chloroform, dimethyl sulfoxide, benzene, toluene and the like. Of these, dimethylsulfoxide, chloroform and toluene are preferable.

The reaction temperature for this reaction is not particularly limited, and is generally 20 to 90° C., preferably 30 to 80° C.

The charged molar ratio of the dibasic acid or anhydride thereof relative to compound (3) is preferably not less than 1-fold relative to $k_2$ of the object phospholipid derivative (1), more preferably within the range of 2- to 10-fold, particularly preferably within the range of 2- to 5-fold.

In this reaction, a catalyst generally used for an esterification reaction may also be used. While the kind of the catalyst is not particularly limited, for example, comparatively mild basic catalysts such as triethylamine, pyridine, dimethylaminopyridine, dimethyl-4-amino-2-methylpyridine, ammonium 4-pyrrolidinopyrrolidineacetate, sodium phosphate, sodium carbonate, sodium hydrogen carbonate, sodium borate, sodium acetate and the like are preferably used.

In this way, phospholipid derivative (1) of the present invention can be produced. The obtained phospholipid derivative (1) can be purified by methods known per se such as chromatography, dialysis, recrystallization and the like.

3. Liposome Containing Phospholipid Derivative (1)

Phospholipid derivative (1) of the present invention can be used as a constituent component of a liposome, like known lipids having a membrane forming ability. In the liposome containing phospholipid derivative (1) of the present invention (hereinafter to be referred to as "the liposome of the present invention"), unlike conventionally-used liposomes, when in contact with a low pH (near pH 5-7) environment in the endosome in the cell, the liposome membrane is unstabilized, and therefore, it is efficiently fused with the endosome membrane, and the contents of the liposome is efficiently transferred into the cytoplasm. Therefore, the liposome of the present invention has pH-sensitiveness, and can have a cell introduction rate more improved than known drug carriers (therefore, the liposome of the present invention may be sometimes referred to as "the pH-sensitive liposome of the present invention").

A lipid constituting the liposome of the present invention together with phospholipid derivative (1) may be any of phospholipids and lipids other than phospholipid, as long as it has a membrane forming ability. Examples of such lipid include natural or synthetic phospholipids such as phosphatidylcholine (PC), phosphatidylethanolamine (PE), phosphatidylserine (PS), phosphatidylinositol (PI), phosphatidylglycerol (PG), phosphatidic acid (PA), dicetyl phosphate, stearylamine, sphingomyelin (SPM), cardiolipin and the like, or partial or full hydrogen additive thereof; natural lecithins such as soybean lecithin, corn lecithin, cottonseed oil lecithin, egg-yolk lecithin and the like, which are mixtures of the phospholipids or hydrogen additive thereof; hydrogenated soybean lecithin, hydrogenated egg-yolk lecithin, phospholipid derivatives wherein polyethylene glycol, an aminoglycan or a fluorescent group is introduced into these phospholipids, and the like. The hydrocarbon group at the 1-position and 2-position of these lipid are the same or different, and is constituted with the above-mentioned acyl group having 8-24 carbon atoms, an aliphatic hydrocarbon group having 8-24 carbon atoms, and the like. Among the above-mentioned lipids, one or more kinds are used in a mixture.

The liposome of the present invention can suppress flowability of the liposome membrane and further enhance time-course stability of the liposome itself by adding sterols or saccharides such as glycerol, sucrose and the like, as a stabilizer. Examples of the above-mentioned sterol include cholesterol, phytosterol, dihydrocholesterol, cholesteryl stearate, cholesteryl nonanoate, cholesteryl hydroxystearate, dihydrocholesteryl oleate and the like. The sterol is preferably cholesterol, phytosterol or cholesteryl stearate.

In addition, as an antioxidant, tocopherol homolog, i.e., vitamin E and the like may also be added to the liposome. Tocopherol includes 4 isomers of $\alpha$, $\beta$, $\gamma$ and $\delta$, and any tocopherol can be used in the present invention.

The liposome of the present invention can also further contain a dendron-bearing lipid to enhance pharmacological activity. Since a dendron-bearing lipid has a proton sponge effect, escape from the endosome can be accelerated and transgene activity can be enhanced.

In the liposome of the present invention, phospholipid derivative (1) is preferably contained in 1-50 mol %, more preferably 2-30 mol %, of the whole starting materials used for liposome production.

Particularly, when $R^3$ of the formula (1) is a 2-methylpropylene group, it is preferably contained in 8-30 mol %, particularly preferably 10-30 mol %. When $R^3$ is a 2-cyclohexene group, it is preferably contained in 2-20 mol %, particularly preferably 2-12 mol %. When the addition ratio of phospholipid derivative (1) is 1-50 mol % of the whole liposome, the liposome formation property becomes superior and the obtained liposome shows good pH-sensitiveness.

The liposome of the present invention can be produced by, for example, mixing phospholipid derivative (1), a lipid (e.g., phospholipid) and any of the above-mentioned components according to a technique known for the production of liposome, and treating the mixture by a method such as sonication method, French Press method, reversed-phase evaporation method, surfactant method, extrusion method, calcium-EDTA chelate method, freeze-thawing method and the like, or by an emulsifiers such as a vacuum emulsifier, a high-pressure homomixer, a microfluidizer, manton-gaulin and the like.

In addition, the liposomes are subjected to a sizing operation such as filtering, gel filtration and the like, liposomes having a uniform particle size can be selectively obtained, whereby the stability of the liposome can be further enhanced.

Since the particle size of the liposome also influences the stability thereof as mentioned above, the liposome of the present invention is desirably processed by the above-mentioned operations to have a uniform particle size. While the weight average particle size and number average particle size are generally used for indicating the particle size of liposome, the weight average particle size is desirable from the aspect of retention volume of the liposome. The weight average particle size of the liposome of the present invention is generally 20 nm-800 nm, preferably 40-500 nm, more preferably 80 nm-400 nm.

To obtain the above-mentioned desirable particle size, an extrusion filtration method and the like may be used, which filtrate off liposomes having large particle size by passing through a filter having a predetermined pore size.

By enclosing any pharmacologically active substance or diagnostic medicament in the thus-obtained liposome, the pharmacologically active substance or the diagnostic medicament can be easily transported into the cell. The method of enclosing the pharmacologically active substance or diagnostic medicament is not particularly limited, and an inclusion method known per se can be appropriately employed. Generally, by mixing a large excess pharmacologically active substance or diagnostic medicament during liposome formation, a liposome enclosing the pharmacologically active substance or diagnostic medicament can be obtained.

While the pharmacologically active substance that can be enclosed in the liposome of the present invention is not particularly limited as long as it does not impair the liposome formation, and examples thereof include physiologically active substances such as nucleic acid, polynucleotide, gene and analogs thereof, glycosaminoglycan and a derivative thereof, oligosaccharide, polysaccharide and derivatives thereof, protein, peptide and the like; anti-inflammatory agent, steroid, anti-cancer agent, enzyme drug, antibiotic, antioxidant, lipid uptake inhibitor, hormone drug, angiotensin converting enzyme inhibitor, angiotensin receptor antagonist, growth migration inhibitor of smooth muscle cell, platelet aggregation inhibitor, chemical mediator liberation inhibitor, growth factor or inhibitor of vascular endothelial cell, aldose reductase inhibitor, mesangial cell proliferation inhibitor, lipoxygenase inhibitor, immunosuppressant, immunostimulator, antiviral drug, anticoagulant, vasodilator, Maillard's reaction inhibitor, amyloidosis inhibitor, NOS inhibitor, AGES inhibitor and radical scavenger and the like.

While the diagnostic medicament that can be enclosed in the liposome of the present invention is not particularly limited as long as it does not impair the liposome formation, and examples thereof include intracorporeal diagnostic drugs such as radiographic contrast agent, radioisotope-labeled nuclear medicine diagnostic drug, diagnostic drug for nuclear magnetic resonance diagnosis and the like, and labels such as water-soluble fluorescence dye and the like.

While the pH of the living body is generally not less than 7 (e.g., pH of blood is about 7.4), since the inside of the endosome in the cell is in acidic conditions (generally pH 5-7, preferably pH 5-6), the liposome of the present invention shows membrane fusion property. Particularly, the liposome of the present invention gains hydrophobicity at pH 5-7 to be unstable, and shows pH-sensitiveness permitting easy membrane fusion. Thus, when the liposome of the present invention is taken up by the cell due to endocytosis, the pH of the periphery of the liposome decreases to near pH 5-7 due to the action of proton pump, and the liposome of the present invention then expresses membrane fusion property and is fused with the endosome membrane. As a result, the substance contained in the liposome is released to the cytoplasm.

That is, the liposome of the present invention is a pH-sensitive liposome as well as a liposome playing a role of a DDS carrier to a biological cell.

EXAMPLES

The present invention is explained in more detail in the following by referring to Examples. However, the present invention is not limited by the Examples.

<<Production of Phospholipid Derivative (1)>>

Phospholipid derivative (1) of the present invention, which is an important constituent component of the liposome of the present invention, was produced as follows.

Example 1

Synthesis of Octaglycerolglutaryl Distearoylphosphatidylethanolamine 3-Methylglutaric Acid Derivative (Hereinafter to be Indicated as DSPE-MGluPG8G) (Dibasic Acid Introduction Rate 58.9%)

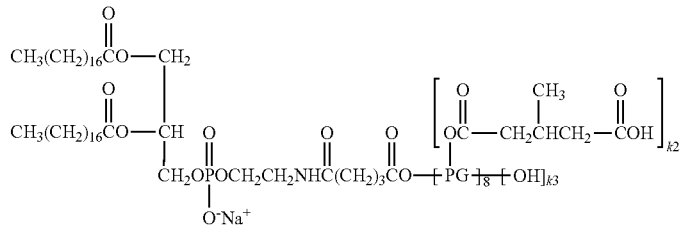

(4)

To octaglycerolglutaryl distearoylphosphatidylethanolamine (manufactured by NOF CORPORATION, SUNBRIGHT DSPE-PG8G) (2.0 g, 1.38 mmol) was added dimethylformamide (20 mL) as a solvent, and the amine was dissolved at 80° C. Then, 3-methylglutaric anhydride (4.78 g, 37.3 mmol) was added thereto, and the mixture was reacted with stirring at 80° C. for 6 hr. The reaction solution was evaporated to dryness under vacuum, and the obtained crystals were dispersed in ion exchange water (175 mL) and methanol (30 mL).

The dispersion was enclosed with a dialysis membrane Spectra/Pro6 (manufactured by Spectrum Laboratories Inc.), and dialyzed against ion exchange water (8 L) for 3 days. The ion exchange water was changed every other day. The solution after dialysis was freeze-dried to give the object DSPE-MGluPG8G (1.4 g).

From $^1$H-NMR (deuterated chloroform/deuterated methanol=4/1 weight ratio solvent), the protons of the terminal methyl group of the stearoyl group at δ0.88 (integrated value 6.0), the protons of the branched methyl group of the 3-methylglutaric acid at δ1.04 (integrated value 16.0), the protons of the methylene group of the stearoyl group at δ1.26 (integrated value 60.0), the protons of the methylene group and the methine group of the 3-methylglutaric acid-derived —CH$_2$CH(CH$_3$)CH$_2$—, the protons of the methylene group of the stearoyl group (—CH$_2$CH$_2$COO—), and the protons of the methylene group of the glutaric acid residue (—NHCO—

CH$_2$CH$_2$CH$_2$COO—) at δ2.2-2.5 (integrated value 33.6), and the protons of the octaglycerol-derived methylene group and methine group, the protons of the methylene group of the ethanolamine moiety —OCH$_2$CH$_2$—NH—, and the protons of the methylene group contained in DSPE backbone (—CH—CH$_2$—OPO$_3$—) at δ3.2-4.5 (integrated value 53.1) were confirmed.

Since the integrated value of the protons of the methyl group at δ1.04 is 16, it was confirmed that average 5.3 out of 9 hydroxyl groups contained in the octaglycerol backbone were substituted by 3-methylglutaric acid. That is, k2 and k3 in the above-mentioned formula (4) were 5.3 and 3.7, respectively. Accordingly, the dibasic acid introduction rate is 5.3/9×100=58.9%.

Example 2

Synthesis of Octaglycerolglutaryl Distearoylphosphatidylethanolamine 3-Methylglutaric Acid Derivative (Hereinafter to be Indicated as DSPE-MGluPG8G) (Dibasic Acid Introduction Rate 100%)

To octaglycerolglutaryl distearoylphosphatidylethanolamine (manufactured by NOF CORPORATION, SUNBRIGHT DSPE-PG8G) (2.0 g, 1.38 mmol) was added toluene (47 mL) as a solvent, and the amine was dissolved at 40° C. 3-Methylglutaric anhydride (2.39 g, 18.7 mmol) and N-methylmorpholine (2.08 mL, 18.9 mmol) were added thereto, and the mixture was reacted with stirring at 40° C. for 5 hr. Acetonitrile (200 ml) was added to the reaction solution, and the mixture was ice-cooled to precipitate crystals. Thereafter, it was filtered, and the obtained crystals were washed twice with acetonitrile (200 mL) and dried to give the object DSPE-MGluPG8G (1.9 g).

The dibasic acid introduction rate was calculated in the same manner as in Example 1. As a result, k2 and k3 were 9.0 and 0, respectively. Accordingly, the introduction rate is 9/9×100=100%.

Example 3

Synthesis of Octaglycerolglutaryl Distearylphosphatidylethanolamine 1,2-Cyclohexanedicarboxylic Acid Derivative (Hereinafter to be Indicated as DSPE-CHexPG8G) (Introduction Rate 56.7%)

To octaglycerolglutaryl distearoylphosphatidylethanolamine (manufactured by NOF CORPORATION, SUNBRIGHT DSPE-PG8G) (2.0 g, 1.38 mmol) was added toluene (47 mL) as a solvent, the amine was dissolved at 50° C. Cyclohexanedicarboxylic anhydride (2.01 g, 13.0 mmol) and sodium acetate (1.1 g, 13.0 mmol) were added thereto, and the mixture was reacted with stirring at 30° C. for 1 hr. The reaction solution was diluted with chloroform (200 mL), and sodium acetate was removed by filtration. Furthermore, the filtrate was evaporated to dryness under vacuum, and the obtained crystals were dissolved in chloroform (50 mL). Acetonitrile (200 mL) was added thereto and the crystals were precipitated. It was filtered, and the obtained crystals were washed twice with acetonitrile (200 mL) and dried to give the object DSPE-CHexPG8G (2.1 g).

From $^1$H-NMR (deuterated chloroform solvent), the protons of the terminal methyl group of the stearoyl group at δ0.88 (integrated value 6.0), the protons of the methylene group of the stearoyl group at δ1.26 (integrated value 59.0), the protons of the cyclohexanedicarboxylic acid-derived methylene group, the protons of the methylene group of the stearoyl group (—CH$_2$CH$_2$COO—) and the protons of the methylene group of glutaric acid residue (—NHCO—CH$_2$CH$_2$CH$_2$COO—) at δ1.3-2.2 (integrated value 51.8), and the proton of the cyclohexanedicarboxylic acid-derived methine group at δ2.6-3.0 (integrated value 10.1) were confirmed.

Since the integrated value of the protons of the methyl group at δ2.6-3.0 is 10.1, it was confirmed that average 5.1 out of 9 hydroxyl groups contained in the octaglycerol backbone were substituted by cyclohexanedicarboxylic acid. That is, k2 and k3 in the above-mentioned formula (5) were 5.1 and 3.9, respectively. Accordingly, the dibasic acid introduction rate is 5.1/9×100=56.7%.

Example 4

Synthesis of Octaglycerolglutaryl Distearylphosphatidylethanolamine 1,2-Cyclohexanedicarboxylic Acid Derivative (Hereinafter to be Indicated as DSPE-CHexPG8G) (Introduction Rate 95.6%)

To octaglycerolglutaryl distearoylphosphatidylethanolamine (manufactured by NOF CORPORATION, SUNBRIGHT DSPE-PG8G) (3.0 g, 2.06 mmol) was added toluene (70 mL) as a solvent, and the amine was dissolved at 50° C. Cyclohexanedicarboxylic anhydride (8.62 g, 55.9 mmol) and sodium acetate (4.7 g, 55.9 mmol) were added thereto, and the mixture was reacted with stirring at 50° C. for 6 hr. The presence of a new spot of the reaction product was confirmed by TLC, the disappearance of octaglycerolglutaryl distearoylphosphatidylethanolamine as the starting material (5)

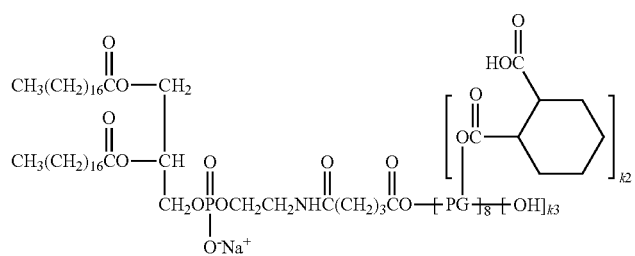

was confirmed by TLC, and the reaction was completed. The reaction solution was diluted with chloroform (300 mL), and sodium acetate was removed by filtration. Furthermore, the filtrate was evaporated to dryness under vacuum, and the obtained crystals were dissolved in chloroform (100 mL).

Acetonitrile (300 mL) was added thereto, and the crystals were precipitated. It was filtered, and the obtained crystals were washed twice with acetonitrile (300 mL) and dried to give the object DSPE-CHexPG8G (3.45 g).

The introduction rate was calculated in the same manner as in Example 3. As a result, k2 and k3 were 8.6 and 0.4, respectively. Accordingly, the dibasic acid introduction rate is 8.6/9×100=95.6%.

<<Preparation of Liposome>>

Using the phospholipid derivatives obtained in Examples 1-4, liposomes were prepared.

Example 5

Preparation of EYPC/DSPE-MGluPG8G (Introduction Rate 58.9%)=50/50(Wt) [73/27 (Mol)] Liposome Egg-yolk phosphatidylcholine (manufactured by NOF CORPORATION, COATSOME NC-50, hereinafter to be indicated as "EYPC", 100 mg) was dissolved in chloroform (10 ml) to give an EYPC solution (concentration 10 mg/ml). Separately, the DSPE-MGluPG8G (introduction rate 58.9%, 100 mg) obtained in Example 1 was dissolved in chloroform (10 ml) to give a DSPE-MGluPG8G (introduction rate 58.9%) solution (concentration 10 mg/ml).

The EYPC solution (500 μl) and DSPE-MGluPG8G solution (500 μl) obtained above were charged in a 10 ml eggplant-shaped flask, and chloroform was evaporated by a rotary evaporator under reduced pressure to form an EYPC/DSPE-MGluPG8G (73:27 (molar ratio)) thin film.

Then, a trisodium 8-hydroxypyrene-1,3,6-trisulfonate which is a water-soluble fluorescence dye (hereinafter to be indicated as pyranine) (18.9 mg), p-xylene-bis-pyridium bromide (DPX), which is a quenching agent molecule thereof (23.8 mg), and disodium hydrogen phosphate (9.9 mg) were dissolved in distilled water (0.98 ml), and then 1N aqueous sodium hydroxide solution (0.02 ml) was added thereto to adjust the mixture to pH 7.4 to give an aqueous fluorescence quenching solution. This aqueous fluorescence quenching solution (0.85 ml) was poured into the eggplant-shaped flask in which the aforementioned EYPC/DSPE-MGluPG8G thin film was formed, and ultrasonic irradiation was applied thereto by a bath type ultrasonic irradiation apparatus for 30 sec to disperse the lipid membrane to give a dispersion. The dispersion was subjected to freezing and thawing treatment 3 times to form a liposome. The particle size of the liposome was unified to 100 nm using an extruder equipped with a polycarbonate membrane having a pore size of 100 nm. This was purified by a column filled with agarose gel (manufactured by GE Healthcare Japan Co., Glutathione Sepharose 4B) to give a pyranine and DPX-enclosing EYPC/DSPE-MGluPG8G (73:27 (molar ratio)) liposome solution.

The lipid concentration of the obtained liposome solution was 1.87 mmol/l as measured by Test Wako (manufactured by Wako Pure Chemical Industries, Ltd.).

Example 6

Preparation of EYPC/DSPE-MGluPG8G (Introduction Rate 58.9%)=75/25 (Wt) [89/11 (Mol)] Liposome According to the procedures described in Example 5 except that an EYPC/DSPE-MGluPG8G (89:11 (molar ratio)) thin film was formed by changing the solution amounts of the EYPC solution (500 μl) and DSPE-MGluPG8G (introduction rate 58.9%) solution (500 μl) both described in Example 5 to EYPC solution (750 μl) and DSPE-MGluPG8G (introduction rate 58.9%) solution (250 μl), respectively, a pyranine-enclosing EYPC/DSPE-MGluPG8G (89:11 (molar ratio)) liposome solution was obtained.

The lipid concentration of the obtained liposome solution was 4.32 mmol/l as measured by Test Wako (manufactured by Wako Pure Chemical Industries, Ltd.).

Example 7

Preparation of EYPC/Dope/DSPE-MGluPG8G (Introduction Rate 58.9%)=25/25/50 (Wt) [36/38/26 (Mol)] Liposome Solution Dioleoylphosphatidylethanolamine (COATSOME ME-8181 manufactured by NOF CORPORATION, hereinafter to be indicated as DOPE, 100 mg) was dissolved in chloroform (10 ml) to give a DOPE solution (concentration 10 mg/ml).

According to the procedures described in Example 3 except that an EYPC/DOPE/DSPE-MGluPG8G (36:38:26 (molar ratio)) thin film was formed by using EYPC solution (250 μl), DOPE solution (250 μl) and DSPE-MGluPG8G (introduction rate 58.9%) solution (500 μl) instead of the EYPC solution (500 μl) and DSPE-MGluPG8G (introduction rate 58.9%) solution (500 μl) both described in Example 5, a pyranine-enclosing EYPC/DOPE/DSPE-MGluPG8G (36:38:26 (molar ratio)) liposome solution was obtained.

The lipid concentration of the obtained liposome solution was 1.69 mmol/l as measured by Test Wako (manufactured by Wako Pure Chemical Industries, Ltd.).

Example 8

Preparation of EYPC/DSPE-MGluPG8G (Introduction Rate 100%)=45/55(Wt) [73/27 (Mol)] Liposome The DSPE-MGluPG8G (introduction rate 100%, 100 mg) obtained in Example 2 was dissolved in chloroform (10 ml) to give a DSPE-MGluPG8G (introduction rate 100%) solution (concentration 10 mg/ml).

According to the procedures described in Example 5 except that an EYPC/DSPE-MGluPG8G (73:27 (molar ratio)) thin film was formed by using EYPC solution (450 μl) and DSPE-MGluPG8G (introduction rate 100%) solution (550 μl) instead of the EYPC solution (500 μl) and DSPE-MGluPG8G (introduction rate 58.9%) solution (500 μl) both described in Example 5, a pyranine-enclosing EYPC/DSPE-MGluPG8G (73:27 (molar ratio)) liposome solution was obtained.

The lipid concentration of the obtained liposome solution was 1.16 mmol/l as measured by Test Wako (manufactured by Wako Pure Chemical Industries, Ltd.).

Example 9

Preparation of EYPC/DSPE-MGluPG8G (Introduction Rate 100%)=71/29(Wt) [89/11 (Mol)] Liposome According to the procedures described in Example 5 except that an EYPC/DSPE-MGluPG8G (89:11 (molar ratio)) thin film was formed by using EYPC solution (710 μl) and DSPE-MGluPG8G (introduction rate 100%) solution (290 μl) instead of the EYPC solution (500 μl) and DSPE- MGluPG8G (introduction rate 58.9%) solution (500 µl) both described in Example 5, a pyranine-enclosing EYPC/DSPE-MGluPG8G (89:11 (molar ratio)) liposome solution was obtained.

The lipid concentration of the obtained liposome solution was 2.48 mmol/l as measured by Test Wako (manufactured by Wako Pure Chemical Industries, Ltd.).

Example 10

Preparation of EYPC/DSPE-CHexPG8G (Introduction Rate 56.7%)=74/26(Wt) [89/11 (Mol)] Liposome Solution The DSPE-CHexPG8G (introduction rate 56.7%, 100 mg) obtained in Example 3 was dissolved in chloroform (10 ml) to give a DSPE-CHexPG8G (introduction rate 56.7%) solution (concentration 10 mg/ml).

The EYPC solution (740 µl, concentration 10 mg/ml) described in Example 5 and the above-mentioned DSPE-CHexPG8G (introduction rate 56.7%) solution (260 µl) were charged in a 10 ml eggplant-shaped flask, and chloroform was evaporated under reduced pressure by a rotary evaporator to form an EYPC/DSPE-CHexPG8G (89:11 (molar ratio)) thin film. Then, pyranine (18.9 mg), DPX (23.8 mg) and disodium hydrogen phosphate (9.9 mg) were dissolved in distilled water, and the mixture was adjusted to pH 8.0 with 1N aqueous sodium hydroxide solution to give an aqueous fluorescence quenching solution in a total amount of 1 ml. Then, according to the procedures described in Example 5 except the above, a pyranine-enclosing EYPC/DSPE-CHexPG8G (89:11 (molar ratio)) liposome solution was obtained.

The lipid concentration of the obtained liposome solution was 3.32 mmol/l as measured by Test Wako (manufactured by Wako Pure Chemical Industries, Ltd.).

Example 11

Preparation of EYPC/DSPE-CHexPG8G (Introduction Rate 56.7%)=82/18(Wt) [93/7 (Mol)] Liposome Solution According to the procedures described in Example 10 except that an EYPC/DSPE-CHexPG8G (93:7 (molar ratio)) thin film was formed by changing the solution amounts of the EYPC solution (740 µl) and DSPE-CHexPG8G (introduction rate 56.7%) solution (260 µl) both described in Example 10 to EYPC solution (820 µl) and DSPE-CHexPG8G (introduction rate 56.7%) solution (180 µl), a pyranine-enclosing EYPC/DSPE-CHexPG8G (93:7 (molar ratio)) liposome solution was obtained.

The lipid concentration of the obtained liposome solution was 3.32 mmol/l as measured by Test Wako (manufactured by Wako Pure Chemical Industries, Ltd.).

Example 12

Preparation of EYPC/DSPE-CHexPG8G (Introduction Rate 95.6%)=79/21(Wt) [93/7 (Mol)] Liposome Solution The DSPE-CHexPG8G (introduction rate 95.6%, 100 mg) obtained in Example 4 was dissolved in chloroform (10 ml) to give a DSPE-CHexPG8G (introduction rate 95.6%) solution (concentration 10 mg/ml).

According to the procedures described in Example 10 except that an EYPC/DSPE-CHexPG8G (93:7 (molar ratio)) thin film was formed by using EYPC solution (790 µl) and DSPE-CHexPG8G (introduction rate 95.6%) solution (210 µl) instead of the EYPC solution (740 µl) and DSPE-CHexPG8G (introduction rate 56.7%) solution (260 µl) both described in Example 10, a pyranine-enclosing EYPC/DSPE-CHexPG8G (93:7 (molar ratio)) liposome solution was obtained.

The lipid concentration of the obtained liposome solution was 1.91 mmol/l as measured by Test Wake (manufactured by Wake Pure Chemical Industries, Ltd.).

Example 13

Preparation of EYPC/DSPE-CHexPG8G (Introduction Rate 95.6%)=90/10(Wt) [97/3 (Mol)] Liposome Solution According to the procedures described in Example 10 except that an EYPC/DSPE-CHexPG8G (97:3 (molar ratio)) thin film was formed by using EYPC solution (900 µl) and DSPE-CHexPG8G (introduction rate 95.6%) solution (100 µl) instead of the EYPC solution (740 µl) and DSPE-CHexPG8G (introduction rate 56.7%) solution (260 µl) both described in Example 10, a pyranine-enclosing EYPC/DSPE-CHexPG8G (97:3 (molar ratio)) liposome solution was obtained.

The lipid concentration of the obtained liposome solution was 2.61 mmol/l as measured by Test Wako (manufactured by Wako Pure Chemical Industries, Ltd.).

Comparative Example 1

Preparation of EYPC Liposome Solution

An EYPC solution (1000 µl) was charged in an eggplant-shaped flask instead of the EYPC solution (500 µl) and DSPE-MGluPG8G solution (500 µl) both described in Example 5, and chloroform was evaporated under reduced pressure by a rotary evaporator to form an EYPC thin film. Hereafter, according to the procedures described in Example 5, a pyranine-enclosing EYPC liposome solution was obtained. The lipid concentration of the obtained liposome solution was 1.56 mmol/l as measured by Test Wako (manufactured by Wako Pure Chemical Industries, Ltd.).

[Measurement Test of pH-Sensitiveness of Liposome>>

Using the liposomes prepared in Examples 5-13 and Comparative Example 1, pH-sensitiveness measurement tests were performed.

Example 14

Measurement of pH-Sensitiveness of Liposome Obtained in Example 5

To the liposome solution obtained in Example 5 was added phosphate buffered saline (hereinafter to be indicated as "PBS") to adjust the lipid concentration of the liposome to 1.6 mmol/l. The PBS (2469 µl) adjusted to a given pH with 1N hydrochloric acid was placed in a quartz cell, a liposome dispersion (31 µl) was added thereto at 37° C. to adjust the lipid concentration to 20 µmol/l. After incubation at 37° C. for 15 min, fluorescence intensity ($F_{15min}$) was measured. In addition, 10% aqueous Triton X-100 (manufactured by Sigma-Aldrich Japan Co. Ltd.) solution (25 µl) was added thereto, and the mixture was stirred, and the fluorescence intensity ($F_{max}$) was measured.

The release (%) was calculated by the following formula.

$$\text{release } (\%) = \frac{F_{15min} - F_0}{F_{max} - F_0} \times 100$$

$F_{15min}$: fluorescence intensity at 15 min after liposome addition
$F_0$: fluorescence intensity at t=0 by measurement with PBS at pH 7.4
$F_{max}$: fluorescence intensity after addition of Triton Example 15

Measurement of pH-Sensitiveness of Liposome Obtained in Example 6

In the same manner as in Example 14 except that the liposome solution obtained in Example 6 was used instead of the liposome solution obtained in Example 5, the release % at a given pH was measured.

Example 16

Measurement of pH-Sensitiveness of Liposome Obtained in Example 7

In the same manner as in Example 14 except that the liposome solution obtained in Example 7 was used instead of the liposome solution obtained in Example 5, the release % at a given pH was measured.

Example 17

Measurement of pH-Sensitiveness of Liposome Obtained in Example 8

In the same manner as in Example 14 except that the liposome solution obtained in Example 8 was used instead of the liposome solution obtained in Example 5, the release % at a given pH was measured.

Example 18

Measurement of pH-Sensitiveness of Liposome Obtained in Example 9

In the same manner as in Example 14 except that the liposome solution obtained in Example 9 was used instead of the liposome solution obtained in Example 5, the release % at a given pH was measured.

Example 19

Measurement of pH-Sensitiveness of Liposome Obtained in Example 10

In the same manner as in Example 14 except that the liposome solution obtained in Example 10 was used instead of the liposome solution obtained in Example 5, the release % at a given pH was measured.

Example 20

Measurement of pH-Sensitiveness of Liposome Obtained in Example 11

In the same manner as in Example 14 except that the liposome solution obtained in Example 11 was used instead of the liposome solution obtained in Example 5, the release % at a given pH was measured.

Example 21

Measurement of pH-Sensitiveness of Liposome Obtained in Example 12

In the same manner as in Example 14 except that the liposome solution obtained in Example 12 was used instead of the liposome solution obtained in Example 5, the release % at a given pH was measured.

Example 22

Measurement of pH-Sensitiveness of Liposome Obtained in Example 13

In the same manner as in Example 14 except that the liposome solution obtained in Example 13 was used instead of the liposome solution obtained in Example 5, the release % at a given pH was measured.

Comparative Example 2

Measurement of pH-Sensitiveness of Liposome Obtained in Comparative Example 1

In the same manner as in Example 14 except that the liposome solution obtained in Comparative Example 1 was used instead of the liposome solution obtained in Example 5, the release % at a given pH was measured.

The lipid compositions of the liposome solutions used in Examples 14-22 and Comparative Example 2 (each derived from the liposome solutions obtained in Examples 5-13 and Comparative Example 1) are as shown in each of the following Tables.

TABLE 1

| pH-sensitiveness | | Ex. 14 | Ex. 16 | Ex. 22 | Comp. Ex. 2 |
|---|---|---|---|---|---|
| preparation of liposome solution | | Ex. 5 | Ex. 7 | Ex. 13 | Comp. Ex. 1 |
| lipid composition (mol %) | EYPC | 73 | 36 | 97 | 100 |
| | DOPE | — | 38 | — | — |
| | DSPE-MGluPG8G | 27 | 26 | — | — |
| | DSPE-CHexPG8G | — | — | 3 | — |

The results of the pH-sensitiveness measurements in Example 14, Example 16, Example 22 and Comparative Example 2 are as shown in FIG. 1.

As the results, the liposome of Comparative Example 1 did not release a fluorescent substance contained in the liposome without responding pH, however the liposomes of Example 5, Example 7 and Example 13 release the fluorescent substance contained in the liposome responded to pH. Particularly, the liposome containing phospholipid derivative (1) of the present invention at high ratio showed pH-sensitive in low pH.

TABLE 2

| pH-sensitiveness | | Ex. 14 | Ex. 15 | Ex. 17 | Ex. 18 | Comp. Ex. 2 |
|---|---|---|---|---|---|---|
| preparation of liposome solution | | Ex. 5 | Ex. 6 | Ex. 8 | Ex. 9 | Comp. Ex. 1 |
| lipid composition (mol %) | EYPC | 73 | 89 | 73 | 89 | 100 |
| | DSPE-MGluPG8G (introduction rate 58.9%) | 27 | 11 | — | — | |
| | DSPE-CHexPG8G (introduction rate 100%) | — | — | 27 | 11 | |

Figure 2:
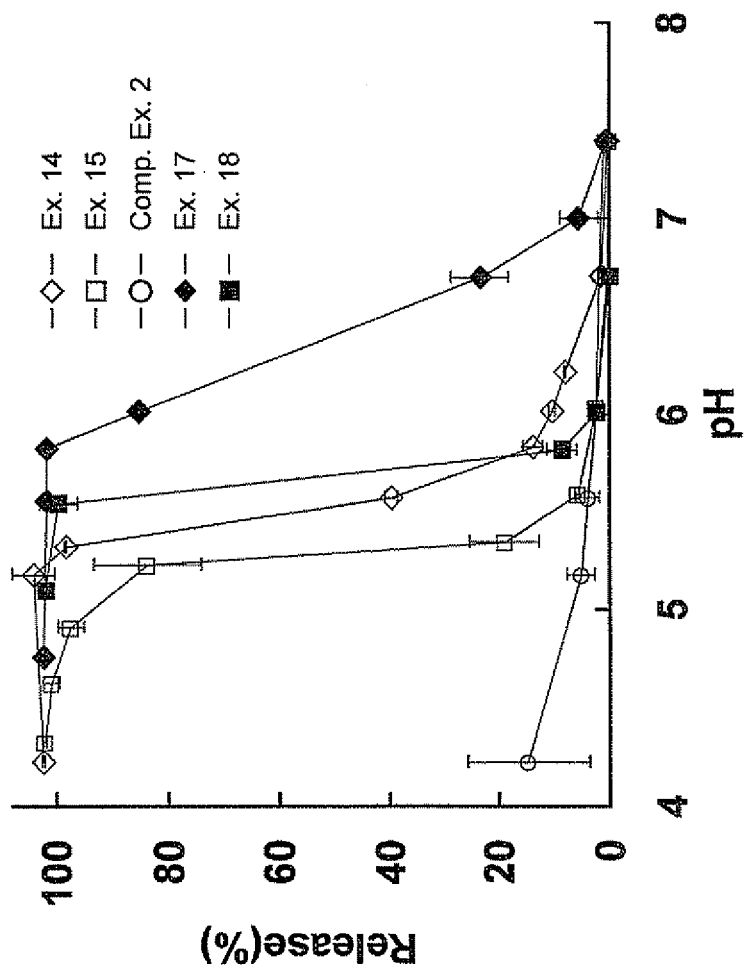
FIG. 2 shows that the liposome of the present invention containing DSPE-MGluPG8G is taken up by a cell and releases the substance in the liposome.

The measurement results of the pH-sensitiveness of Examples 14-15, Examples 17-18 and Comparative Example 2 are as shown in FIG. 2.

As a result, the liposome of Comparative Example 1 did not respond to pH and did not release the fluorescent substance in the liposome. However, the liposomes of Examples 5-6 and Examples 8-9 responded to pH to release the fluorescent substance in the liposome.

When Examples 14 and 15 having a dibasic acid introduction rate of 58.9% are compared, and when Examples 17 and 18 having a dibasic acid introduction rate of 100%, as the lipid composition of the liposome became decrease, the pH-sensitive region shifted to the acidic side when the dibasic acid introduction rate was the same. In addition, when Examples 14 and 17 having a lipid composition of 27 mol % are compared, and when Examples 15 and 18 having a lipid composition of 11 mol % are compared, as the dibasic acid introduction rate became lower, the pH-sensitive region shifted to the acidic side when the lipid composition rate was the same.

TABLE 3

| pH-sensitiveness | | Ex. 19 | Ex. 20 | Ex. 21 | Ex. 22 |
|---|---|---|---|---|---|
| preparation of liposome solution | | Ex. 10 | Ex. 11 | Ex. 12 | Ex. 13 |
| lipid composition (mol %) | EYPC | 89 | 93 | 93 | 97 |
| | DSPE-CHexPG8G (introduction rate 56.7%) | 11 | 7 | — | — |
| | DSPE-CHexPG8G (introduction rate 95.6%) | — | — | 7 | 3 |

Figure 3:
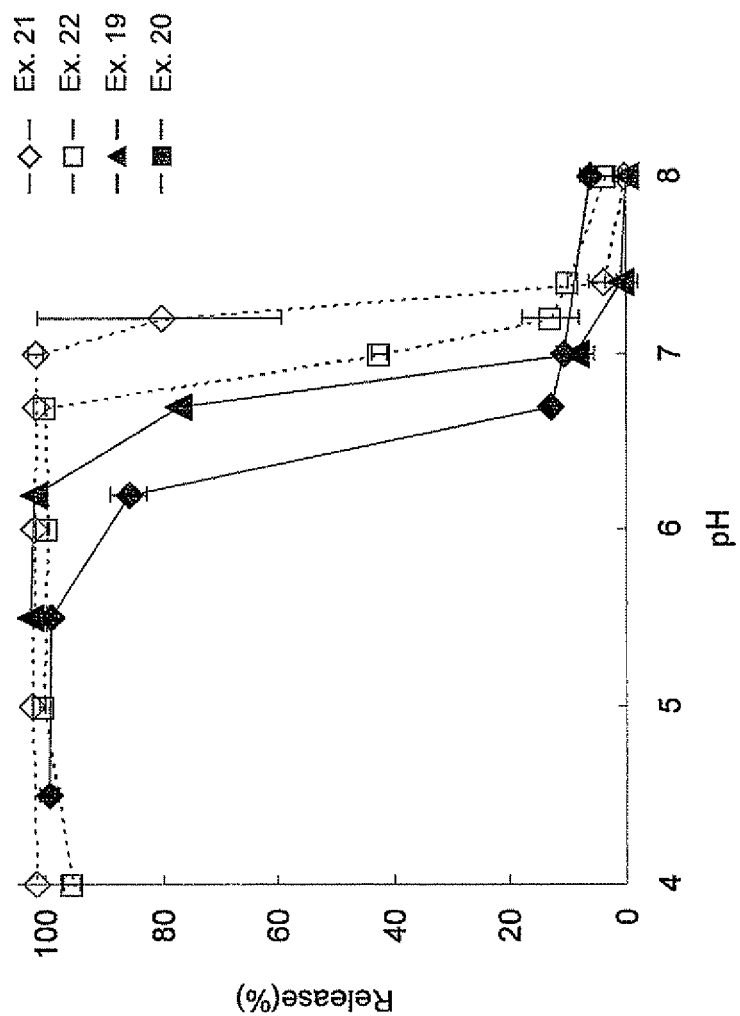
FIG. 3 shows that the liposome of the present invention containing DSPE-CHexPG8G is taken up by a cell and releases the substance in the liposome.

The measurement results of the pH-sensitiveness of Examples 19-22 are as shown in FIG. 3.

As a result, the liposomes of Examples 10-13 responded to pH and released the fluorescent substance in the liposome.

When Examples 19 and 20 having a dibasic acid introduction rate of 56.7%, and when Examples 21 and 22 having a dibasic acid introduction rate of 95.6% are compared, as the lipid composition of the liposome became decrease, the pH-sensitive region shifted to the acidic side when the dibasic acid introduction rate was the same. In addition, In comparison with Examples 20 and 21 having a lipid composition of 7 mol %, as the dibasic acid introduction rate became lower, the pH-sensitive region shifted to the acidic side when the lipid composition rate was the same.

When Example 15 in Table 2 and Example 19 in Table 3 are compared, DSPE-CHexPG8G showed stronger pH sensitive property.

<<Measurement of Uptake Ability of Liposome Solution into Cell>>

The uptake ability of the liposome of the present invention into a cell was confirmed by the following experiments.

Example 23

Preparation of EYPC/DSPE-MGluPG8G=50/50 (Wt)+Rh-PE 0.1 Mol % Liposome Solution

Egg-yolk phosphatidylcholine (COATSOME NC-50 manufactured by NOF CORPORATION, hereinafter to be indicated as EYPC, 100 mg) was dissolved in chloroform (10 ml) to give an EYPC solution (concentration 10 mg/ml). N-lisamine rhodamine B sulfonyl dipalmitoylphosphatidylethanolamine (manufactured by Avanti Polar Lipids Inc., hereinafter to be indicated as Rh-PE, 10 mg) was dissolved in chloroform (10 ml) to give an Rh-PE solution (concentration 1 mg/ml). Separately, the DSPE-MGluPG8G (100 mg) obtained in Example 1 was dissolved in chloroform (10 ml) to give a DSPE-MGluPG8G solution (concentration 10 mg/ml).

The EYPC solution (500 μl), Rh-PE solution (10 μl) and DSPE-MGluPG8G solution (500 μl) were charged in a 50 ml eggplant-shaped flask, and chloroform was evaporated by a rotary evaporator under reduced pressure to form an EYPC/DSPE-MGluPG8G/Rh-PE thin film. Then, pyranine (18.9 mg), DPX (23.8 mg) and disodium hydrogen phosphate (9.9 mg) were dissolved in distilled water (0.98 ml), and then 1N aqueous sodium hydroxide solution (0.02 ml) was added thereto to adjust the mixture to pH 7.4 to give an aqueous fluorescence quenching solution.

This aqueous fluorescence quenching solution (0.85 ml) was charged in an eggplant-shaped flask in which the aforementioned EYPC/DSPE-MGluPG8G thin film was formed, and ultrasonic irradiation was applied thereto by a bath type ultrasonic irradiation apparatus for 30 sec to disperse the lipid membrane to give a dispersion. The dispersion was subjected to freezing and thawing treatment 3 times to form a liposome, after which it was applied to a treatment using an extruder equipped with a polycarbonate membrane having a pore size of 100 nm to unify the particle size of the liposome to 100 nm. This was purified by a column filled with agarose gel (manufactured by GE Healthcare Japan Co., Sepharose 4B) to give an aqueous fluorescence quenching solution-enclosing EYPC/DSPE-MGluPG8G/Rh-PE (73:27:0.1 (molar ratio)) liposome solution.

The lipid concentration of the obtained liposome solution was 1.50 mmol/l as measured by Test Wako (manufactured by Wako Pure Chemical Industries, Ltd.).

Example 24

Preparation of EYPC/DSPE-MGluPG8G-70/30(Wt)+Rh-Pe 0.1 Mol % Liposome Solution

According to the procedures described in Example 23 except that an EYPC/DSPE-MGluPG8G/Rh-PE thin film was formed by using EYPC solution (700 μl), Rh-PE solution (13 μl) and DSPE-MGluPG8G solution (300 μl) instead of the EYPC solution (500 μl), Rh-PE solution (10 μl) and DSPE-MGluPG8G solution (500 μl) described in Example 23, a fluorescence quenching aqueous solution-enclosing EYPC/DSPE-MGluPG8G/Rh-PE (87:13:0.1 (molar ratio)) liposome solution was obtained.

The lipid concentration of the obtained liposome solution was 1.76 mmol/l as measured by Test Wako (manufactured by Wako Pure Chemical Industries, Ltd.).

Comparative Example 3

Preparation of EYPC+Rh-PE (0.1 Mol %) Liposome Solution

According to the procedures described in Example 23 except that an EYPC thin film was formed by using EYPC solution (1000 μl) and Rh-PE solution (16 μl) instead of the EYPC solution (500 μl), Rh-PE solution (13 μl) and DSPE-MGluPG8G solution (500 μl) described in Example 23, a fluorescence quenching aqueous solution-enclosing EYPC/Rh-PE (100:0.1 (molar ratio)) liposome solution was obtained.

The lipid concentration of the obtained liposome solution was 3.85 mmol/l as measured by Test Wako (manufactured by Wako Pure Chemical Industries, Ltd.).

Example 25

Measurement of Cell Uptake Ability of Liposome Solution Obtained in Example 23

To the liposome solution obtained in Example 23 was added phosphate buffered saline to adjust the lipid concentration of the liposome to 1 mmol/l, and the resulting mixture was passed though an acetyl cellulose membrane with a pore size of 200 nm to give a diluted liposome solution. Separately, a medium (RPMI1640, 10% FBS, 500 μl) was added to DC2.4 cells (100,000) washed twice with Hank's saline (Hank's Balanced Salt Solution), and the mixture was cultured for 2 days. Thereto was added the aforementioned diluted liposome solution (500 μl), and the mixture was incubated at 37° C. for 4 hr to allow liposome to be taken up by the cells. Thereafter, microscope observation was performed and the fluorescence intensity was measured by a flow cytometer (FCM).

The fluorescence intensity at 15 min after addition of the liposome was measured, and the release (%) was calculated based on the fluorescence intensity when Triton was finally added as 100%.

Example 26

Measurement of Cell Uptake Ability of Liposome Solution Obtained in Example 24

In the same manner as in Example 25 except that the liposome solution obtained in Example 24 was used instead of the liposome solution obtained in Example 23, the cell uptake ability was measured.

Comparative Example 4

Measurement of Cell Uptake Ability of Liposome Solution Obtained in Example 3

In the same manner as in Example 25 except that the liposome solution obtained in Example 3 was used instead of the liposome solution obtained in Example 23, the cell uptake ability was measured.

The measurement results of the cell uptake ability obtained in Example 25 and 26, and Comparative Example 4 are shown in FIG. 4 and Table 4.

TABLE 4

| measurement of cell uptake ability | | Ex. 25 | Ex. 26 | Comp. Ex. 4 |
|---|---|---|---|---|
| liposome solution | | Ex. 23 | Ex. 24 | Comp. Ex. 3 |
| lipid composition (mol ratio) | EYPC | 73 | 87 | 100 |
| | Rh-PE | 0.1 | 0.1 | 0.1 |
| | DSPE-MGluPG8G | 27 | 13 | — |

TABLE 4-continued

| measurement of cell uptake ability | | Ex. 25 | Ex. 26 | Comp. Ex. 4 |
|---|---|---|---|---|
| fluorescence intensity (relative value) | pyranine-derived | 9.8 | 7.8 | 1.0 |
| | rhodamine B-derived | 4.4 | 3.2 | 0.8 |

When the liposome of Comparative Example 3 free of phospholipid derivative (1) of the present invention was used, only a slight amount of not only the liposome membrane-derived fluorescent substance (rhodamine B) but also a fluorescent substance (pyranine) in the liposome was taken up into the cell. However, when the liposomes of Examples 23 and 24 containing phospholipid derivative (1) of the present invention were used, all fluorescent substances were taken up into the cell.

<<Tumor Rejection Test by Drug Delivery Using Liposome>>

The drug delivery ability of the liposome of the present invention was confirmed by the following experiments.

Example 27

Preparation of Liposome Dispersion Used for Tumor Rejection Test

Egg-yolk phosphatidylcholine (EYPC), and a solution of DSPE-MGluPG8G (introduction rate 100%) described in Example 2 in chloroform or a solution of DSPE-CHexPG8G (introduction rate 95.6%) described in Example 4 in methanol were charged in a flask at a given molar ratio (EYPC alone, EYPC/DSPE-MGluPG8G=69/31, EYPC/DSPE-CHexPG8G=97/3, mol/mol), and then a solution of monophosphoryl lipid A (MPLA, Sigma) in chloroform was added thereto at 4 g/mol lipids. The solvent was evaporated under reduced pressure by a rotary evaporator and the residue was placed under high vacuum for 2 hr to remove the residual organic solvent.

Dulbecco's phosphate buffered saline (pH 8.0) containing ovalbumin (OVA, Sigma) at 4 mg/ml was added to the obtained mixed thin film at 4 mg OVA/10 μmol lipids, and the mixture was vigorously stirred under ice-cooling using a vortex mixer to detach the thin film. The pH of the solution was appropriately measured and aqueous NaOH solution was added as necessary to always maintain pH 7.4 or above. The solution was subjected to freezing and thawing treatment 5 times, after which the solution was passed through a polycarbonate membrane having a pore size of 100 nm using an extruder to unify the particle size of the liposome.

The solution was passed through Sepharose 4B column equilibrated with Dulbecco's phosphate buffered saline (pH 7.4) to purify the liposomes, after which the lipid concentration was quantified by Test WakoC. In addition, to the lipid dispersion (40 μl) was added 2-isopropanol (60 μl) to dissolve the liposome, and the OVA concentration of the obtained dispersion was quantified using Coomassie Protein Assay Kit (Pierce). The dispersion was centrifuged by Optima TLX (Beckman coulter) at 55000 rpm under ice-cooling for 3 hr, and buffer was added to adjust the OVA concentration of the liposome dispersion to 100 μg OVA/100 μl.

Example 28

Tumor Rejection Test of Mouse Immunized with Liposome Dispersion 7-week-old C57BL/6 female mice were purchased from Oriental Yeast Co. Ltd. The OVA/100 μl liposome dispersion obtained in Example 27 and OVA/PBS solution were subcutaneously administered to the back of the mice at 100 μg per mouse twice every week. One week later, OVA expression cancer cell E.G7-OVA cell was subcutaneously administered to the back at $10^6$/mouse, and the time course changes of the tumor growth was monitored. The tumor volume was obtained by the following formula.

Tumor volume(mm³)=0.5×A×B² (A:major axis(mm), B: minor axis(mm))

In addition, E.G7-OVA cells were also inoculated to untreated mice and used as a control of tumor growth.

The results of the tumor rejection test are shown in FIG. 5.

As a result, three liposome dispersions of EYPC, EYPC/DSPE-MGluPG8G=69/31 and EYPC/DSPE-CHexPG8G=97/3 were compared to find that EYPC/DSPE-MGluPG8G and EYPC/DSPE-CHexPG8G containing phospholipid derivative (1) of the present invention suppressed the tumor growth, whereby it was clarified that tumor is rejected by subcutaneous immunity. Particularly, EYPC/DSPE-CHexPG8G completely rejected the tumor.

INDUSTRIAL APPLICABILITY

The liposome of the present invention shows a more improved cell introduction rate than known drug carriers since it is efficiently fused with the endosome membrane and can efficiently transfer the contents of the liposome into the cytoplasm.

The pH-sensitive liposome of the present invention can express membrane fusion property at a lesion site, and can efficiently and safely introduce a drug into an affected area or cell. Therefore, the pH-sensitive liposome of the present invention, which encloses a pharmacologically active substance, a physiologically active substance or a diagnostic substance, is useful as DDS and vaccine for treatment and diagnostic objects.

This application is based on patent application No. 2009-260398 filed in Japan (filing date: Nov. 13, 2009), the contents of which are incorporated in full herein.

The invention claimed is:

1. A phospholipid derivative represented by the following formula (I)

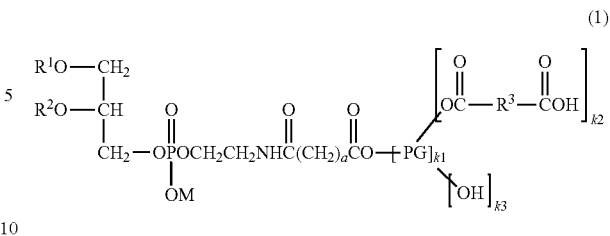

wherein
R¹ and R² are each independently an acyl group having 8-24 carbon atoms or an aliphatic hydrocarbon group having 8-24 carbon atoms,
R³ is a branched chain or cyclic divalent hydrocarbon group having 2-12 carbon atoms,
a is an integer of 0-5,
M is a hydrogen atom, an alkali metal or an ammonio group,
PG is a residue derived from polyglycerol,
k1 is an integer of 2-50, and
k2≧k3 and k2+k3=k1+1 are satisfied.

2. The phospholipid derivative according to claim 1, wherein R¹ and R² are each independently an acyl group having 12-20 carbon atoms or an aliphatic hydrocarbon group having 12-20 carbon atoms.

3. The phospholipid derivative according to claim 1, wherein R³ is a branched chain or cyclic divalent hydrocarbon group having 3 to 8 carbon atoms.

4. The phospholipid derivative according to claim 3, wherein R³ is a 2-methylpropylene group or a 1,2-cyclohexene group.

5. A liposome comprising the phospholipid derivative according to claim 1.

6. The liposome according to claim 5, which is pH-sensitive.

7. A liposome comprising the phospholipid derivative according to claim 2.

8. The liposome according to claim 7, which is pH-sensitive.

9. A liposome comprising the phospholipid derivative according to claim 3.

10. The liposome according to claim 9, which is pH-sensitive.

11. A liposome comprising the phospholipid derivative according to claim 4.

12. The liposome according to claim 11, which is pH-sensitive.

* * * * *